United States Patent [19]

Julemont

[11] 4,402,688
[45] Sep. 6, 1983

[54] DISPOSABLE DIAPER WITH CONTOURED ELASTIC

[75] Inventor: Jean Julemont, Stembert, Belgium

[73] Assignee: Colgate-Palmolive, New York, N.Y.

[21] Appl. No.: 315,387

[22] Filed: Oct. 27, 1981

[51] Int. Cl.³ .............................................. A41B 13/02
[52] U.S. Cl. .................................................... 604/385
[58] Field of Search ............... 128/284, 286, 287, 288, 128/290 R, DIG. 30; 604/366, 370, 372, 378, 385

[56] References Cited

U.S. PATENT DOCUMENTS 4,324,245 4/1982 Mesek et al. ...................... 128/287

FOREIGN PATENT DOCUMENTS 2023431 1/1980 United Kingdom ............... 128/287

Primary Examiner—C. Fred Rosenbaum
Attorney, Agent, or Firm—Norman Blumenkopf; Murray M. Grill; Herbert S. Sylvester

[57] ABSTRACT

A disposable diaper having an absorbent pad between a top sheet and a back sheet. The absorbent pad is contoured to form a crotch area and outwardly extending ears. Bonded to the backing sheet are elastic members which are substantially equally spaced from said crotch area and said ears and run the full length of the diaper. The top sheet is bonded to the backing sheet outwardly of the elastic members.

10 Claims, 2 Drawing Figures

DISPOSABLE DIAPER WITH CONTOURED ELASTIC

BACKGROUND OF THE INVENTION

1. Field of the Invention

This invention relates to disposable diapers and more particularly to a contoured elasticized diaper.

2. Description of the Prior Art

In the past, elasticized contoured diapers have been developed such as that disclosed in U.S. Pat. No. 3,860,003, issued Jan. 14, 1975 for "Contractable Side Portions for Disposable Diapers" wherein elastic strips are secured outwardly of the absorbent pad of the diaper. In this patent and as in those diapers currently being commercially utilized, the elastic members extend the full length of the diaper but are only secured in the crotch aeas of the diaper, thus utilizing only a portion of the elastic members while wasting the unsecured portions.

Furthermore, by securing the elastic members only in the crotch area, no provision was made for the ear portions when diapering an infant. The elastic in the crotch area will tend to facilitate the diapering procedure. However, the ears would lie loosely.

The present invention overcomes the waste of elastic material by securing the elastic members throughout their entire length thus utilizing elastic material heretofore wasted while also urging opposed pairs of ears towards each other thus further facilitating diapering an infant.

SUMMARY OF THE INVENTION

In carrying out the invention, a contoured diaper of substantially hour-glass shape is formed of an absorbent pad between a backing sheet and a top sheet. The pad is hour glass in shape having a crotch area and opposed pairs of ears. Elastic members substantially equally spaced from the crotch area and the ears and substantially parallel to the crotch area and the ears are adhesively secured to the backing sheet throughout substantially their entire length. The top sheet is heat sealed to the backing sheet preferably outwardly of the elastic members.

DETAILED DESCRIPTION OF THE INVENTION

Figure 1:
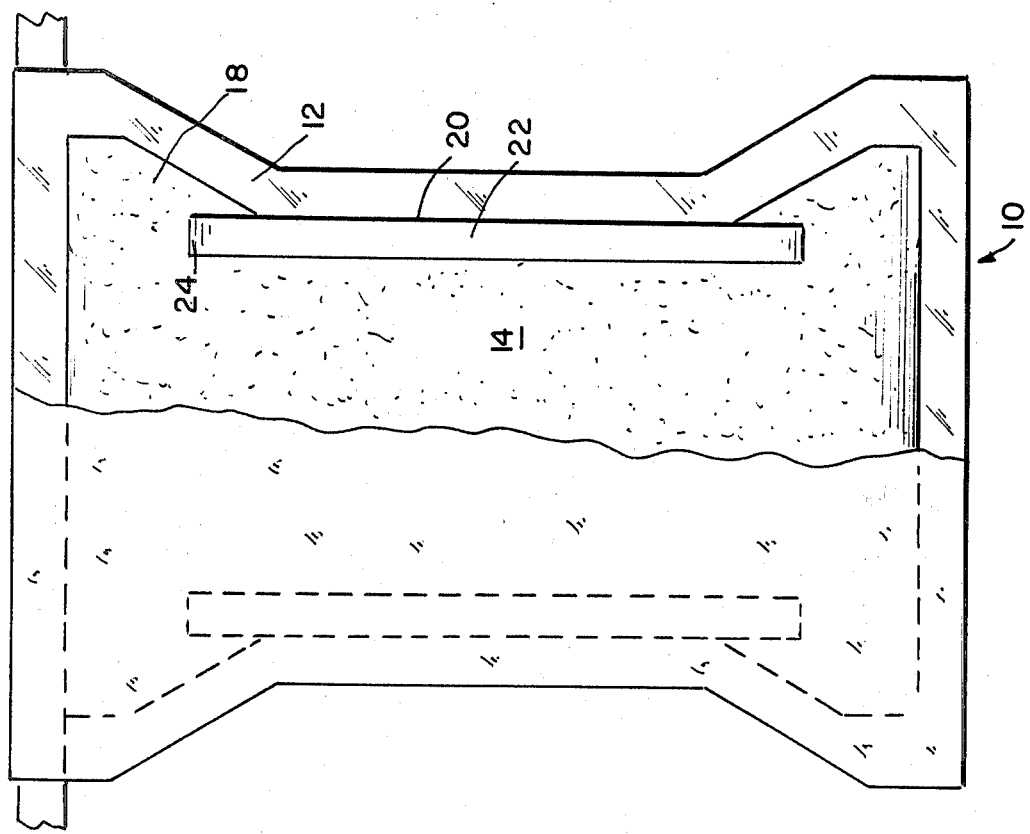
FIG. 1 is a plan view of an elasticized contour diaper constructed in accordance with the prior art; and, FIG. 2 is a planview of a contoured elasticized diaper constructed in accordance with the concepts of the present invention.
Figure 2:
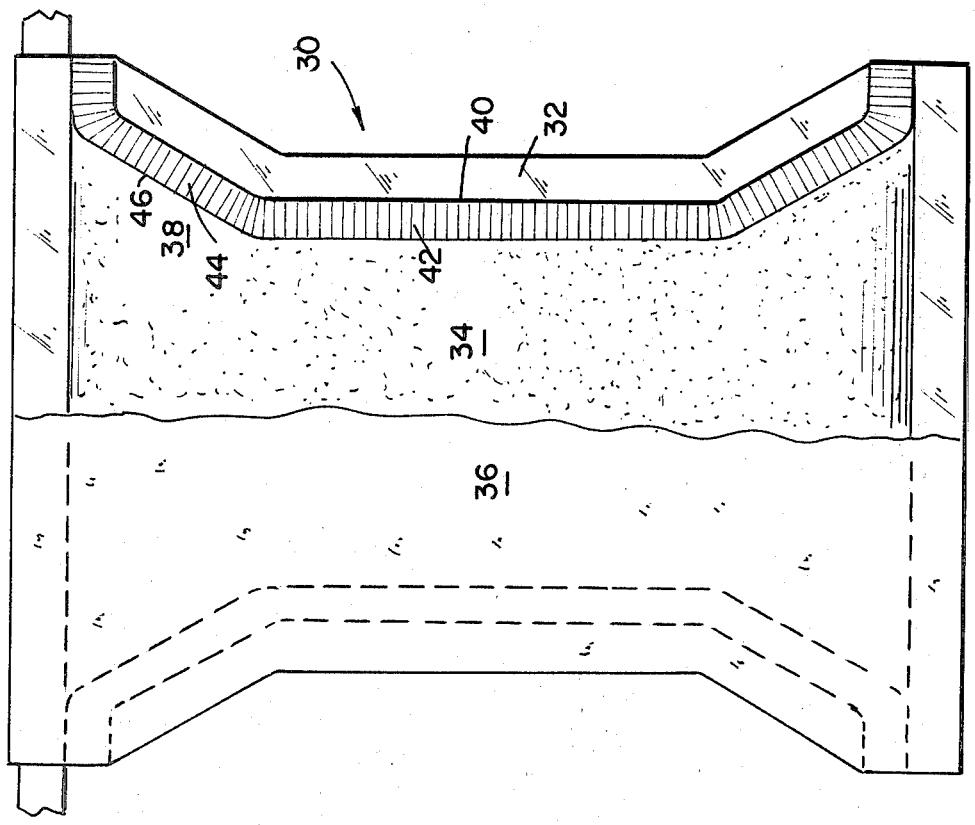

With continuing reference to the accompanying drawing, reference numeral 10 generally designates a contoured elasticized diaper generally employing the principles of the prior art. The diaper 10 includes a backing sheet 12 on which a contoured absorbent pad 14 is disposed. Overlying the pad is a top sheet 16. The absorbent pad 14 is contoured to form opposed pairs of ears 18 and a crotch area 20. Elastic members 22 are secured to the backing sheet 12 only at the crotch area wasting the free ends 24 of the elasticized material of the elastic members.

The elasticized contoured diaper according to the present invention is generally designated by reference numeral 30 and is of an hour-glass configuration and includes a backing sheet 32 of a waterproof material, such as an impervious polyethylene or the like. An absorbent pad 34 is disposed on the backing sheet 32 and a top sheet 36 overlies the absorbent pad 34. The top sheet is preferably constructed of non-woven polyethylene or polypropylene fibers.

The absorbent pad 34 is formed of suitable absorbent material such as wood fluff or the like. The absorbent pad 34 is of an hour-glass configuration having opposed pairs of ears 38 and a crotch area 40, the ears being at the four corners of the diaper 30. Wadding sheet may be disposed on, under or about the absorbent pad 34.

A pair of elastic members 42 of an elasticized strip material are provided. The backing sheet 32, the absorbent pad, or both are provided with adhesive lines or spots on their upper surfaces and the elastic members 40 are thus secured to the backing sheet 32 throughout their entire length both being parallel to the crotch area 40 and the ears 38. The elastic members 42 are closely spaced from the absorbent pad 34.

The elastic members 42 are bonded to the backing sheet 32 while in a stretched state. The top sheet 36 is bonded to the backing sheet 32 along the peripheral edges of the diaper 30 and outwardly of the elastic members 42 preferably by heating sealing, hot melt or suitable adhesions.

Since the elastic members 42 are bonded to the backing sheet along their full length, the portions 44 parallel to the ears 38 will cause opposed pairs of ears 38 to extend towards each other when diapering an infant, thus facilitating the diapering process.

In use, any suitable tabs which may be provided with self-stick adhesive may be used to hold the diaper on the infant by securement thereof to the ears of the diaper 30.

What is claimed is:

1. A disposable diaper comprising a backing sheet, an absorbent pad on said backing sheet, a top sheet overlying said absorbent pad and secured to said backing sheet, said absorbent pad being of an hour-glass shape defining a central crotch area and ears spaced from said crotch area, said ears including contoured portions extending outwardly and towards the ends of said diaper, opposed side elastic members secured to said backing sheet along two opposite side edges thereof and extending substantially parallel to said crotch area and parallel to said contoured portions and extending outwardly along said ears and to said ends of said diaper for facilitating securement of the diaper on an infant.

2. A disposable diaper according to claim 1, wherein said elastic members are substantially equally spaced from said crotch area and said contoured portions.

3. A disposable diaper according to claim 1, wherein said elastic members are waterproof forming fluid seals.

4. A disposable diaper according to claim 1, wherein said elastic members are bonded to said backing sheet along their full length.

5. A disposable diaper according to claim 1, wherein said top sheet is bonded to said backing sheet outwardly of said elastic members.

6. A disposable diaper according to claim 5, wherein said top sheet is heat sealed to said backing sheet.

7. A disposable diaper according to claim 1, wherein said elastic members are substantially equally spaced from said crotch area and said contoured portions and are secured to said backing sheet.

8. A disposable diaper according to claim 7, wherein said elastic members extend the full length of the diaper and are adhesively secured to said backing sheet along their full length while under tension.

9. A disposable diaper according to claim 8, wherein said top sheet is heat sealed to said backing sheet.

10. A disposable diaper according to claim 8, wherein said top sheet is heat sealed to said backing sheet outwardly of said elastic members.

* * * * *